(12) United States Patent
Weiss et al.

(10) Patent No.: US 8,318,468 B2
(45) Date of Patent: Nov. 27, 2012

(54) EMULSIONS IN ENZYMATIC REACTIONS

(75) Inventors: Albrecht Weiss, Langenfeld (DE); Michael Mueller, Monheim (DE); Eric Dubreucq, Montpellier (FR); Guy Moulin, Montferrier-sur-Lez (FR)

(73) Assignee: Cognis IP Management GmbH, Duesseldorf (DE)

( * ) Notice: Subject to any disclaimer, the term of this patent is extended or adjusted under 35 U.S.C. 154(b) by 142 days.

(21) Appl. No.: 12/853,657

(22) Filed: Aug. 10, 2010

(65) Prior Publication Data

US 2010/0323415 A1 Dec. 23, 2010

Related U.S. Application Data

(62) Division of application No. 10/595,101, filed as application No. PCT/EP2004/008770 on Aug. 5, 2004, now abandoned.

(30) Foreign Application Priority Data

Aug. 14, 2003 (DE) .................................. 103 37 451

(51) Int. Cl.
*C12N 9/96* (2006.01)

(52) U.S. Cl. ........ 435/188; 435/195; 435/196; 435/197; 435/198

(58) Field of Classification Search .................. 435/188, 435/195, 196, 197, 198
See application file for complete search history.

(56) References Cited

U.S. PATENT DOCUMENTS 3,939,260 A * 2/1976 Lafon .......................... 424/401
4,839,287 A 6/1989 Holmberg et al.

FOREIGN PATENT DOCUMENTS

| DE | 19923785 A1 * | 11/2000 |
| JP | 2000-270886 A | 3/2000 |
| JP | 2003-500046 A | 1/2003 |
| JP | 2003-033195 A | 4/2003 |
| WO | 91/00918 | 1/1991 |
| WO | 2000-71676 A1 | 11/2000 |

OTHER PUBLICATIONS

English machine translation of DE 19923785 downloaded from the EPO on Nov. 3, 2009; 12 pages.*
Orlich et al., "Candida Rugose lipase reactions in nonionic w/o-microemulsion with a technical surfactant", Enzyme and Microbial Technology, 2001, vol. 2, pp. 42-48.
Drauz et al., "Enzyme Catalysis in Organic Synthesis", VCH-Verlag, Weinheim, 1975, complete book.
Foerster et al., "Calculation of Optimum Emulsifier Mixtures for Phase Inversion Emulsification", Intl. Journal of Cosmetic Science, 1994, vol. 16, pp. 84-92.
Japanese Office Action from Application No. 522960/2006 dated Apr. 6, 2010.

* cited by examiner

*Primary Examiner* — Susan Hanley
(74) *Attorney, Agent, or Firm* — Diehl Servilla LLC

(57) ABSTRACT

A reaction medium for enzyme-catalyzed reactions is provided, comprising an oil-in-water emulsion including water, an emulsifier, an oil phase and at least one interfacially active enzyme, where the emulsion is produced by the phase inversion temperature process and has a droplet size of 50 to 400 nm. A method for the enzyme-catalyzed esterification, transesterification or hydrolysis of fatty acid alkyl esters and/or triglycerides is also provided where the oil-in-water emulsion is used as the reaction medium.

8 Claims, No Drawings

EMULSIONS IN ENZYMATIC REACTIONS

CROSS-REFERENCE TO RELATED APPLICATIONS

This application is a division of U.S. application Ser. No. 10/595,101, now abandoned, filed Apr. 16, 2007 which is a U.S. National Stage application under 35 U.S.C. §371 from International Application No. PCT/EP2004/008770 which has an International filing date of Aug. 5, 2004, which designated the United States of America and which claims priority from German Patent Application number DE 103 37 451.5 filed Aug. 14, 2003, all of which are hereby incorporated by reference in their entireties.

FIELD OF THE INVENTION

This invention relates generally to emulsions, and more particularly to emulsions produced by the phase inversion temperature process and used as a reaction medium for enzyme-catalyzed reactions.

BACKGROUND INFORMATION

Enzymes are being increasingly used as catalysts in chemical and biochemical synthesis. Thus, hydrolases, especially lipases (EC 3.1.1.3), are already being used in many industrial lipolysis processes by virtue of the often milder reaction conditions.

Suitable enzymatic esterification or transesterification processes are described, for example, in K. Drauz and H. Waldmann, Enzyme Catalysis in Organic Synthesis, VCH-Verlag, Weinheim 1975.

It is known that transesterifications in water-free or substantially water-free media are catalyzed by lipases. If water is also present in the reaction system of esters, alcohol and lipases, the elimination of bound acids to free acids normally occurs. Since various lipases also catalyze the formation of esters from free fatty acids and alcohols, a transesterification reaction with an acid intermediate stage is ultimately carried out in the majority of cases in addition to a direct transesterification. For many industrial processes, however, the formation of free acids in the system is a major disadvantage. The water content partly prevents an industrially and commercially acceptable conversion (formation of an nfavourable thermodynamic equilibrium). Expensive industrial equipment has to be used to obtain satisfactory yields (removal of water, for example, by azeotropic distillation, membrane separation processes, vacuum distillation).

The disadvantage of enzyme-catalyzed reactions often lies in the availability and stability of the functional proteins involved in the process. Enzymes stabilized by immobilization, for example by microencapsulation, which can be used for a variety of applications are already known from the prior art.

The reaction of hydrophobic compounds can be carried out by the use of water-in-oil (w/o) microemulsions, as described by Orlich and Schomaeker in Enzyme Microb. Technol.; 2001; 28; 1; 42-48 for the lipase from *Candida rugosa*. However, the concentration of water in the solution and the composition of the components of the w/o microemulsions are very critical to the success of the reaction.

Accordingly, the problem addressed by the present invention was to provide a system for enzyme-catalyzed reactions in which the substrate concentrations could be varied while the interfaces and hence the concentration of oil and water would remain constant to the extent that they would not have a major influence on the reaction or on the activity of the enzyme. In addition, these systems would be inexpensive and recyclable.

BRIEF SUMMARY OF THE INVENTION

An oil in water emulsion including water, an emulsifier and an oil phase is produced by the phase inversion temperature process and has a droplet size of 50 to 400 nm is provided. A process for the enzyme-catalyzed esterification, transesterification or hydrolysis of fatty acid alkyl esters and/or triglycerides is also provided where the oil in water emulsion is used as the reaction medium.

DETAILED DESCRIPTION OF THE INVENTION

The present invention relates to the use of o/w emulsions containing at least water, emulsifiers and an oil phase as a reaction medium for enzyme-catalyzed reactions, the emulsions having been produced by the phase inversion temperature (PIT) process and having a droplet size of 50 to 400 nm.

It has surprisingly been found that o/w emulsions produced by the PIT process satisfy the requirements stated above in excellent fashion.

PIT Emulsions

Emulsions are disperse preparations of at least two liquids insoluble in one another, of which one contains water. Emulsifiers or emulsifier systems are used to homogenize immiscible oil/water phases by emulsification. In the absence of stabilizing emulsifiers, the phases would separate again in view of their different polarities. The amphiphilic emulsifiers sit at the interfaces between the fine droplets and the coherent phase and prevent them from coalescing by steric or electrostatic shielding. Emulsifiers are compounds which join hydrophilic and lipophilic structural units to one another in their molecular structure. The choice and extent of the particular structural units in the emulsifier molecule or emulsifier system affected are often characterized by the hydrophilic/lipophilic balance [HLB (number) value]. As a general rule, emulsifiers or emulsifier systems with comparatively strongly hydrophilic components lead to high HLB values and, in their practical application, generally lead to water-based o/w emulsions with a disperse oil phase. Emulsifiers or emulsifier systems with comparatively strongly lipophilic components lead to comparatively lower HLB values and hence to w/o invert emulsions with a continuous oil phase and a disperse water phase.

It is known that oil-in-water (o/w) emulsions prepared and stabilized with nonionic emulsifiers can undergo generally reversible phase inversion on heating, i.e. the emulsion type changes from o/w to w/o (water-in-oil emulsion) within a certain temperature range. Since the oil becomes the outer continuous phase, the conductivity of the emulsion falls to zero. The mean value of the temperatures between maximal and zero conductivity of the emulsion on heating is called the phase inversion temperature (PIT) and the emulsions thus produced are called PIT emulsions.

It is also known that the position of the PIT depends on a number of factors, for example the nature and phase volume of the oil component, the hydrophilicity and the structure of the emulsifiers and the composition of the emulsifier system.

The droplet size of the PIT emulsion is critically determined by the production process. In general, the water and oil phases are mixed with the emulsifiers and then heated to a temperature above the PIT, the conductivity having to fall to zero. The emulsion is then cooled to the starting temperature (generally room temperature, ca. 20° C.). The emulsion used in accordance with the invention is only formed by the temperature of the emulsion exceeding and then falling below the PIT.

It is known that only those PIT emulsions which form a microemulsion phase with low interfacial tension between oil and water or a lamellar liquid-crystalline phase during phase inversion are characterized by particularly small droplets. The crucial step is always the re-inversion on cooling.

The emulsions according to the invention are distinguished in particular by their droplet fineness. The droplet size is between 50 and 400 nm, preferably in the range from 70 to 300 nm, more preferably in the range from 80 to 250 nm and most preferably in the range from 90 to 160 nm. The droplet sizes are assumed to follow a Gauss distribution. They are measured, for example, by light scattering or absorption.

These fine-droplet emulsions retain their homogeneity through Brownian molecular movement. Brownian molecular movement is a thermal random movement of particles below 5 μm in size. It is the driving force of diffusion and prevents both sedimentation and creaming up (flotation). A major advantage is that the need for energy-intensive stirring can be reduced. It leads to improved diffusion of substrate and enzyme and to reduced energy costs.

The substrate concentrations can be varied without the droplet size having to be reduced. A high substrate concentration can be achieved without any of the droplets coalescing. The low surface tension increases the transfer rate of the molecules at the oil/water interface. The high reproducibility and stability of the PIT emulsions enable biochemical studies to be carried out on enzymes and their reactivity and already known reaction conditions and activities for enzymes to be further optimized.

Besides water, the PIT emulsions also contain an oil phase which contains compounds from the group of fatty acid alkyl esters a) or native vegetable oils and derivatives b). The groups a) and b) are hydrophobic compounds insoluble or only very sparingly soluble in water which may preferably represent the starting materials, i.e. substrates, for the products to be obtained by enzymatic catalysis, but which may also be used as auxiliaries.

Suitable group a) esters are derived in particular from saturated, unsaturated, linear or branched fatty acids containing a total of 7 to 23 carbon atoms. Accordingly, they are compounds corresponding to formula (I):

in which $R^1$ is a $C_{6-22}$ alkyl group and $R^2$ is a $C_{1-4}$ alkyl group, methyl and ethyl groups being particularly preferred. The use of methyl esters is the most advantageous. The methyl esters of formula (I) may be obtained in the usual way, for example by transesterification of triglycerides with methanol and subsequent distillation. Suitable fatty acids are caproic, heptanoic, caprylic, pelargonic, capric, undecanoic, lauric, tridecanoic, myristic, pentadecanoic, palmitic, heptadecanoic, stearic, nonadecanoic, arachic and behenic acid. Unsaturated representatives are, for example, lauroleic, myristoleic, palmitoleic, petroselaidic, oleic, elaidic, ricinoleic, linoleic, conjugated linoleic acid (CLA), more particularly cis9, trans11-CLA or trans10,cis12-CLA, linolaidic, linolenic, conjugated linoleic acid, gadoleic, arachidonic and erucic acid. Mixtures of the methyl and/or ethyl esters of these acids are also suitable. It is particularly preferred to use PIT emulsions which contain methyl and/or ethyl esters from the group consisting of methyl oleate, methyl palmitate, methyl stearate, methyl pelargonate, ethyl oleate, ethyl palmitate, ethyl stearate and/or ethyl pelargonate. However, methyl and/or ethyl esters based on the natural fatty acid mixtures obtained, for example, from linseed oil, coconut oil, palm oil, palm kernel oil, olive oil, castor oil, rapeseed oil, soybean oil or sunflower oil (in the case of rapeseed and sunflower oil, new and old plants) may also be used.

Suitable group b) compounds are native oils of vegetable origin. These are essentially triglycerides and triglyceride mixtures, the glycerol being completely esterified with relatively long-chain fatty acids. Particularly suitable vegetable oils are selected from the group consisting of peanut, coconut and/or sunflower oil.

Important constituents of the PIT emulsions used in accordance with the invention are the emulsifiers and emulsifier systems used. Nonionic emulsifiers, more particularly ethoxylated fatty alcohols and fatty acids, are preferably used as emulsifiers. To form PIT emulsions, it is of advantage to use a two-component emulsifier system containing a hydrophilic emulsifier (A) and a hydrophobic co-emulsifier (B). Suitable hydrophilic nonionic emulsifiers (A) are substances which have an HLB value of about 8 to 18. The HLB value (hydrophilic/lipophilic balance) is a value which may be calculated in accordance with the following equation:

$$HLB=(100-L)/5$$

where L is the percentage by weight of lipophilic groups, i.e. the fatty alkyl or fatty acyl groups in percent in the ethylene oxide addition products.

Fatty alcohol ethoxylates in the context of the teaching according to the invention correspond to formula (II):

in which $R^3$ is a linear or branched, saturated or unsaturated alkyl group containing 6 to 24 carbon atoms and n is a number of 1 to 50. Compounds of formula (II) where n is a number of 1 to 35 and more particularly a number of 1 to 15 are particularly preferred. Other particularly preferred compounds of formula (II) are those where $R^3$ is an alkyl group containing 16 to 22 carbon atoms.

The compounds of formula (II) are obtained in known manner by reaction of fatty alcohols under pressure with ethylene oxide, optionally in the presence of acidic or basic catalysts. Typical examples are caproic alcohol, caprylic alcohol, 2-ethyl hexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or aldehydes from Roelen's oxosynthesis and as monomer fraction in the dimerization of unsaturated fatty alcohols. Technical fatty alcohols containing 12 to 18 carbon atoms, such as for example coconut oil, palm oil, palm kernel oil or tallow fatty alcohol, are preferred.

Fatty acid ethoxylates which may also be used as emulsifier component (A) preferably correspond to formula (III):

where $R^4$ is a linear or branched alkyl group containing 12 to 22 carbon atoms and m is a number of 5 to 50 and preferably 15 to 35. Typical examples are products of the addition of 10 to 30 mol ethylene oxide onto lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils or in the reduction of aldehydes from Roelen's oxosynthesis. Products of the addition of 10 to 30 mol ethylene oxide onto $C_{16-18}$ fatty acids are preferably used.

Partial glycerides which may be used as emulsifier component (B) preferably correspond to formula (IV):

where $COR^5$ is a linear or branched acyl group containing 12 to 22 carbon atoms and x, y and z together stand for 0 or for numbers of 1 to 50 and preferably 15 to 35. Typical examples of partial glycerides suitable for the purposes of the invention are lauric acid monoglyceride, coconut fatty acid monoglyceride, palmitic acid monoglyceride, stearic acid monoglyceride, isostearic acid monoglyceride, oleic acid monoglyceride, conjugated linoleic acid monoglycerides and tallow fatty acid monoglyceride and addition products thereof with 5 to 50 and preferably 20 to 30 mol ethylene oxide. Monoglycerides or technical mono/diglyceride mixtures predominantly containing monoglycerides (IV), where $COR^5$ is a linear acyl group containing 16 to 18 carbon atoms, are preferably used.

Emulsifier mixtures containing components (A) and (B) in a ratio by weight of 10:90 to 90:10, preferably 25:75 to 75:25 and more particularly 40:60 to 60:40 are normally used.

Other suitable emulsifiers are, for example, nonionic surfactants from one of the following groups:
  products of the addition of 2 to 30 mol ethylene oxide and/or 0 to 5 mol propylene oxide onto linear fatty alcohols containing 8 to 22 carbon atoms;
  glycerol monoesters and diesters and sorbitan monoesters and diesters of saturated and unsaturated fatty acids containing 6 to 22 carbon atoms and ethylene oxide adducts thereof;
  alkyl mono- and oligoglycosides containing 8 to 22 carbon atoms in the alkyl group and ethoxylated analogs thereof;
  products of the addition of 15 to 60 mol ethylene oxide onto castor oil and/or hydrogenated castor oil;
  polyol esters and, in particular, polyglycerol esters such as, for example, polyglycerol polyricinoleate or polyglycerol poly-12-hydroxy-stearate. Mixtures of compounds from several of these classes are also suitable;
  products of the addition of 2 to 15 mol ethylene oxide onto castor oil and/or hydrogenated castor oil;
  partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose);
  wool wax alcohols;
  polyalkylene glycols.

The addition products of ethylene oxide and/or propylene oxide onto glycerol mono- and diesters and sorbitan mono- and diesters of fatty acids or onto castor oil are known commercially available products. They are homolog mixtures of which the average degree of alkoxylation corresponds to the ratio between the quantities of ethylene oxide and/or propylene oxide and substrate with which the addition reaction is carried out.

To select suitable emulsifier systems, it can be useful to calculate the PIT of the particular system. However, this also applies in particular to potential optimizations in the choice of the emulsifiers or emulsifier systems and their adaptation to the choice and mixing of aqueous phase on the one hand and the type of oil phase on the other hand as predetermined by other considerations as to technical procedure. Corresponding expert knowledge has been developed in basically totally different fields, particularly in the production of cosmetics. Particular reference is made in this connection to the article by TH. Förster, W. von Rybinski, H. Tesmann and A. Wadle "Calculation of Optimum Emulsifier Mixtures for Phase Inversion Emulsification" in International Journal of Cosmetic Science 16, 84-92 (1994). The article in question contains a detailed account of how the phase inversion temperature (PIT) range of a given three-component system of an oil phase, a water phase and an emulsifier can be calculated by the CAPICO method (calculation of phase inversion in concentrates) on the basis of the EACN value (equivalent alkane carbon number) characteristic of the oil phase. More particularly, this article by Förster et al. cites important literature for the subjects under discussion here which should be viewed in conjunction with the disclosure of this article by Förster et al. With the aid of numerous examples, it is shown how the choice and optimization of the emulsifiers/emulsifier systems are accessible to the adjustment of optimal predetermined values for the phase inversion temperature range by the CAPICO method in conjunction with the EACN concept.

The PIT emulsions used in accordance with the invention preferably contain 20 to 90% by weight of water, more preferably 30 to 80% by weight and most preferably 30 to 60% by weight of water. The balance to 100% by weight is made up of oil phase and emulsifiers and optionally other auxiliaries and additives. The oil phase itself is present in quantities of preferably 10 to 80% by weight and more particularly 40 to 70% by weight. In a preferred embodiment, the oil phase exclusively contains components a) or b) or mixtures of these components. The emulsifiers or emulsifier systems are present in quantities of preferably 1 to 25% by weight, more preferably 5 to 20% by weight and most preferably 5 to 15% by weight. The emulsions used in accordance with the invention preferably have phase inversion temperatures of 20 to 95° C. and more particularly in the range from 30 to 95° C.

The enzymes used in accordance with the invention are interfacially active. Enzymes from the group of hydrolases and/or acyl transferases are preferably used and may be used either on their own or in combination with several enzymes.

Hydrolases selected from the group consisting of esterases, phospholipases, lipases and lipases/acyl transferases are particularly preferred. The latter are interfacially active enzymes which catalyze reactions characteristic of lipases. It has been found that these polypeptides are capable of catalyzing transesterification reactions in the presence of short-chain alcohols for a water content in the reaction mixture which corresponds to a water activity of greater than 0.8. With this water content, a conventional lipase would predominantly catalyze the hydrolysis of the esters in dependence upon the alcohol component. Accordingly, the enzymes in question have characteristic features both for lipases and for acyl transferases. On the basis of sequence homologies to hitherto known enzymes, such as lipase from *Candida parapsilosis* for example, the naturally occurring enzyme according to the invention is a lipase and, on the basis of its enzymatic activity, an acyl transferase.

Typical examples of suitable enzymes, which are not meant to be limiting in any way, are lipases and/or lipases/acyl transferases from organisms selected from the group consisting of *Alcaligenes, Aspergillus niger, Aspergillus oryzea, Aeromonas aerophila, Bacillus* species, *Candida albicans, Candida antarctica (Trychosporon oryzae, Pseudozyma antarctica), Candida antarctica, Candida cylindracea, Candida glabrata, Candida maltosa, Candida parapsilosis, Candida lipolytica, Candida tropicalis, Candida viswanathii, Chromobacterium viscosum, Fusarium solani, Geotrichum candidum, Issatchenkia orientalis (Candida krusei), Kluyveromyces marxianus (C. kefyr, C. pseudotropicalis), Mucor javanicus, Penicilium camemberti, Penicilium roqueforti, Pichia guilliermondii (Candida guilliermondii), Porcine pancreas, Pseudomonas cepacia, Pseudomonas fluorescens, Rhizomucor miehei, Rhizopus arrhizus, Rhizopus oryzae, Rhizopus niveus, Rhizopus javanicus* and *Thermomyces lanugenosus* and mixtures thereof. Lipases and lipases/acyl transferases from the organisms *Alcaligenes, Candida, Chromobacterium, Rhizomucor, Pseudomonas, Rhizopus* and *Thermomyces*, more particularly enzymes from *Candida parapsilosis, Pichia guilliermondii (Candida guilliermondii)* or *Candida antarctica*, are preferred because they are particularly active.

The enzymes to be used in accordance with the invention may be used in various forms. In principle, any supply forms of enzymes known to the expert may be used. In the context of the invention, the definition of "enzyme" also encompasses protein and enzyme protein. Both the enzyme protein and the whole protein, which contains the function of the protein according to the invention in a part of the protein sequence, may be used in accordance with the invention. The enzymes are preferably used in pure form or as a technical enzyme preparation either immobilized on a carrier material and/or in solution, more particularly in aqueous solution, and re-used in so-called repeated batches. Crystallized enzymes, so-called CLECs, obtainable for example from the Altus company, are also preferred. The percentage of active enzyme in the particular technical enzyme preparations varies from manufacturer to manufacturer. However, the average is between 1 and 10% active enzyme.

In another embodiment of the invention, the enzymes to be used in accordance with the invention are used in a quantity of 0.001 to 20% by weight, expressed as pure enzyme or as enzyme preparation, based on the total quantity of oil phase used. More particularly, the quantity to be used is from 0.002 to 1% by weight and, in a particularly preferred embodiment, from 0.002 to 0.2% by weight.

According to the invention, the enzyme-catalyzed reactions are preferably hydrolyses, transesterifications or esterifications, the esterifications being particularly preferred.

According to the invention, cosmetic and/or pharmaceutical products and/or fine chemicals are produced by the enzyme-catalyzed reactions using the PIT emulsion according to the invention. More particularly, carotinoids, sterol-containing oil components and/or vitamin E are produced.

The o/w emulsions according to the invention containing at least water, emulsifiers and an oil phase and produced by the PIT process are eminently suitable for use as a reaction medium for enzyme-catalyzed reactions. Accordingly, the present invention also relates to a process for the enzyme-catalyzed hydrolysis, transesterification or esterification of fatty acid alkyl esters and/or triglycerides, in which o/w emulsions produced by the PIT process are used as the reaction medium. The emulsions used for the process according to the invention correspond in their constituents, conditions and more detailed embodiments to the emulsions which have already been described in detail for the use of these o/w emulsions. Cosmetic and/or pharmaceutical products and/or fine chemicals are preferably produced by the process according to the invention. More particularly, carotinoids, sterol-containing oil components and/or vitamin E are produced. In this process, use may be made of the fact that the water-insoluble substances become soluble in the oil phase of the PIT emulsion and are thus accessible to the enzyme-catalyzed reaction.

According to the invention, the PIT emulsions containing the substrate are added to the reaction vessel containing the immobilized or non-immobilized lipase or lipase/acyl transferase and optionally other auxiliaries and additives. The details of this process, more particularly the quantity of enzyme and the added emulsion, are determined by the nature of the enzyme and the PIT emulsion selected and may be adapted by the expert to suit the particular circumstances. By heating the system, phase separation can be achieved and the emulsifier in the aqueous phase and the product in the oil phase can readily be separated from one another. By using fixed-bed reactors containing the enzyme, the enzyme can be removed and re-used.

The fineness of the oil droplets leads to a large surface between the oil phase and the water phase and thus provides for rapid contact and an increased reaction rate between the enzymes and the oil phase containing the substrates.

In one particular embodiment of this process, the enzymes used are the enzymes already listed for the use of the o/w emulsion according to the invention.

The reaction conditions according to the invention for the enzyme-catalyzed reaction are determined by the optimal reaction range of the enzymes selected and the emulsions used. More particularly, the reaction temperature inter alia is between 15 and 50° C. and preferably between 20 and 40° C. and, more particularly, is 35° C.

The invention will be further described in the following examples, which do not limit the scope of the invention defined by the claims.

EXAMPLES

Production Example H1

Transesterification of oleic acid ethyl ester with methanol or hydrolysis of oleic acid ethyl ester by lipase/acyl transferase and hydrolysis of the oleic acid ester used.

To produce the PIT emulsion of C18:1 oleic acid ethyl ester, a mixture of 0.25 g polyoxyethylene-12-cetylstearyl alcohol (Eumulgin® B1) and 0.2 g polyoxyethylene-6-cetyl alcohol was heated while stirring to 95° C. with 1 g oleic acid ethyl ester and 3 g ultrapure water until all the components had melted. The emulsion was then cooled while stirring to room temperature. The phase inversion temperature (PIT) was approximately 66° C. This emulsion (10 μmol/ml) was added to a solution buffered to pH 6.5 containing lipase/acyl transferase (CPLIP 2) and 2.2 mol/l methanol as substrate and the hydrolysis or the methanolysis was determined in μmol/min/ml in dependence upon the quantity of enzyme [μg/ml]. The results are set out in Table 1.

TABLE 1

| Quantity of enzyme [μg/ml] | Hydrolysis [μmol/min/ml] | Methanolysis [μmol/min/ml] |
|---|---|---|
| 1 | 0.001 | 0.005 |
| 2 | 0.003 | 0.009 |
| 5 | 0.015 | 0.025 |
| 10 | 0.038 | 0.050 |
| 15 | 0.088 | 0.066 |

In addition, the activity of the enzyme in the PIT emulsion containing oleic acid ethyl ester was determined in the presence of methanol or isopropanol. The results are set out in Tables 2 and 3.

TABLE 2

Activity of the enzyme [14 μg/ml] at 45° C.

| Methanol [mol/l] | Hydrolysis [μmol/min/ml] | Methanolysis [μmol/min/ml] |
|---|---|---|
| 0 | 0.089 | 0 |
| 0.5 | 0.037 | 0.024 |
| 1 | 0.024 | 0.034 |
| 2.2 | 0.009 | 0.074 |
| 4 | 0.002 | 0.128 |

TABLE 3

Activity of the enzyme [35 μg/ml] at 30° C.

| Isopropanol [mol/l] | Hydrolysis [μmol/min/ml] | Methanolysis [μmol/min/ml] |
|---|---|---|
| 0 | 0.042 | 0 |
| 0.1 | 0.043 | 0 |
| 0.2 | 0.031 | 0.009 |
| 0.5 | 0.032 | 0.017 |
| 1.0 | 0.027 | 0.046 |
| 1.25 | 0.023 | 0.066 |
| 1.5 | 0.022 | 0.11 |
| 1.75 | 0.020 | 0.17 |
| 2.0 | 0.009 | 0.19 |
| 2.25 | 0.009 | 0.20 |
| 2.5 | 0.0003 | 0.17 |
| 3.0 | 0 | 0.027 |

Discussion of the Results

The results show that both the transesterification of the methanolysis and the hydrolysis can be carried out in a PIT emulsion and that the enzyme does not lose its particular capabilities. The results also show that methanolysis of the PIT emulsion in the presence of water is preferred to hydrolysis.

Transesterification to isopropyl oleate can also be carried out in the system mentioned, the activity of the enzyme showing a maximum at 2.25 mol/l isopropanol.

What is claimed is:

1. A reaction medium for enzyme-catalyzed reactions comprising an oil-in-water (o/w) emulsion, said emulsion comprising:
   (a) water,
   (b) at least one emulsifier,
   (c) an oil phase, and
   (d) at least one interfacially active enzyme,
wherein the emulsion is produced by the phase inversion temperature process and has a droplet size of 50 to 400 nm, and wherein said reaction medium supports an enzyme-catalyzed reaction selected from the group consisting of hydrolysis, esterification and transesterification, and wherein said interfacially active enzyme is pure or present in an enzyme preparation.

2. The reaction medium of claim 1, wherein said interfacially active enzyme comprises a hydrolase and/or an acyl transferase.

3. The reaction medium of claim 2, wherein said hydrolase is selected from the group consisting of esterases, phospholipases, lipases and lipases/acyl transferases.

4. The reaction medium of claim 3, wherein said lipases and/or lipases/acyl transferases are obtained from sources selected from the group consisting of *Alcaligenes, Aspergillus niger, Aspergillus oryzee, Aeromonas aerophila, Bacillus* species, *Candida elbicens, Candida antarctica (Trychosporon oryzee, Pseudozyma antarctica), Candida antarctica, Candida cylindrecee, Candida qtebrete, Candida meltose, Candida perepsllosis, Candida lipotytice, Candida tropicelis, Candida viswenetnit, Chromobacterium viscosum, Fusarium soteni, Geotrichum cendidum, Issatchenkia orientalis (Candida krusei), Kluyveromyces marxianus (C. ketyr, C. pseudotropicalis), Mucor jevenicus, Penicilium cemembetti, Penicilium roqueforti, Pichia guilliermondii (Candida guilliermondii)*, porcine pancreas, *Pseudomonas cepecie, Pseudomonas ftuorescens, Rhizomucor miehei, Rhizopus errbizus, Rhizopus oryzee, Rhizopus niveus, Rhizopus javanicus, Thermomyces lanuginosus* and mixtures thereof.

5. The reaction medium of claim 1, wherein said enzyme is present in an amount of about 0.001 to 20% by weight, based on the total amount of oil phase present.

6. A method of carrying out an enzyme-catalyzed reaction comprising running the reaction in a reaction medium comprising an oil-in-water (o/w) emulsion, said emulsion comprising:
   (a) water,
   (b) at least one emulsifier,
   (c) an oil phase, and
   (d) at least one interfacially active enzyme,
wherein said emulsion is produced by the phase inversion temperature process and has a droplet size of 50 to 400 nm, and wherein said enzyme-catalyzed reaction is selected from the group consisting of hydrolysis, esterification and transesterification, and wherein said interfacially active enzyme is pure or present in an enzyme preparation.

7. The method of claim 6, wherein said interfacially active enzyme comprises a hydrolase and/or an acyl transferase.

8. The method of claim 6, wherein said oil phase comprises compounds selected from the group consisting of fatty acid alkyl esters and triglycerides.

* * * * *